United States Patent
Kreader et al.

(12) 
(10) Patent No.: US 6,699,986 B2
(45) Date of Patent: *Mar. 2, 2004

(54) ELECTROPHORETIC SEPARATION OF NUCLEIC ACIDS FROM PROTEINS AT LOW PH

(75) Inventors: Carol Ann Kreader, Kirkwood, MO (US); John Wesley Backus, Ballwin, MO (US)

(73) Assignee: Ortho-Clinical Diagnostics, Inc., Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/349,387

(22) Filed: Jul. 9, 1999

(65) Prior Publication Data

US 2001/0049437 A1 Dec. 6, 2001

Related U.S. Application Data

(60) Provisional application No. 60/095,258, filed on Aug. 4, 1998.

(51) Int. Cl.[7] ................. C07H 21/00; B01D 57/02; C12Q 1/68; C12P 19/34
(52) U.S. Cl. .................... 536/25.4; 204/462; 435/6; 435/91.2; 536/25.4
(58) Field of Search ................ 536/25.4; 435/6, 435/91.2; 204/462

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,750,982 A | 6/1988 | Tomblin et al. | |
| 4,965,188 A | 10/1990 | Mullis et al. | 435/6 |
| 5,386,024 A | 1/1995 | Kacian et al. | |
| 5,434,270 A | 7/1995 | Ponticello et al. | 548/338.1 |
| 5,523,368 A | 6/1996 | Ponticello et al. | 526/258 |
| 5,582,988 A | 12/1996 | Backus et al. | 435/6 |
| 5,635,045 A * | 6/1997 | Alam | 204/462 |
| 5,973,137 A | 10/1999 | Heath | |

FOREIGN PATENT DOCUMENTS

| | | |
|---|---|---|
| EP | 0 366 438 A1 | 5/1990 |
| EP | 0 611 157 A2 | 8/1994 |

OTHER PUBLICATIONS

Boedtker, H., Methods Enzymol., 1976, vol. 12, Part B, pp. 429–458.*

Smith, J.D., Methods Enzymol., 1976, vol. 12, Part A, pp. 350–361.*

Oehler et al. "beta–Lactamase recovery from *E. coli* cell lystate via two–phase electrophoresis" vol. 12, pp. 873–876, 1996.*

Thomas C. Terwilliger et al., Methylation of Membrane Proteins in Human Erythrocytes, The Journal of Biological Chemistry, vol. 256, No. 6, Issue of Mar. 25, pp. 3067–3076, 1981.

Smith, Robert E. et al.; 1981, Nucleic Acids Research, vol. 9 (20): 5269–5286.

Mirkin, S.M. et al., DNA H Form Requires a Homopurine–Homopyrimidine Mirror Repeat, Nature , vol. 330, Dec. 1987.

George Kalnitsky et al., Some Factors Which Affect the Enzymatic Digestion of Ribonucleic Acid, J. Biol Chem. 234, 1512–1515.

Boom R. et al, Rapid and Simple Method for Purification of Nucleic Acids, Journal of Clinical Microbiology, Mar. vol. No 6, 1990, vol. 28, No. 3, p. 495–503.

Bio–Eureka, New Trends In Bio–Research, Geno Technology, Inc. Gene–Capsul Product Information.

David Moore, Massachusette General Hospital, Preparation of Genomic DNA From Mammalian Tissue, Current Protocols in Molecular Biology, Nov. 24, 1997.

Pier Giorgio Righetti et al, Preparative Isoelectric Focusing Using Immobilized Membranes: Theory History, Hofer Scientific Instruments, Faculty of Pharmacy and Department of Biomedical Sciences and Technologies, University of Milano, Via Celoria 2 Milano; Italy.

Friedrich Helfferich, Iron Exchange, Sell Development Company, Emeryville, California Lecturer at the University of California, Berkeley, p. 162 & 165.

Search Report EP 99 30 6146, dated May 31, 2001.

Carey J. "Gel Retardation of low PH Resolves TRP Repressor–DNA Complexes for Quantitative Study", Proc. Natl. Acad. Sci. USA, vol. 85, pp. 975–979, Feb. 1988.

Friedrich Helfferich, Ion Exchange, McGraw–Hill (1962), pp. 162–163.

Robert K. Scopes, Protein Purification, Principles and Practive, 1982 Springer–Verlag p. 85–86.

Henry R. Mahler, Eugene H. Cordes, Department of Chemistry Indiana University, Biological Chemistry, Second Edition, p. 94.

(List continued on next page.)

*Primary Examiner*—John S. Brusca
*Assistant Examiner*—Shubo Zhou

(57) ABSTRACT

The present invention relates to methods for separating nucleic acids from other cellular debris, especially substances that carry a net positive charge at low pH, by electrophoresis under acid conditions. In the purification method of the present invention, nucleic acids are separated from proteins found in the same biological sample by applying the sample to an electrophesis gel and subjecting the sample to electrophoresis under acid conditions to separate the nucleic acids from the proteins. The optimum pH may differ for different sample types but can be readily determined by those skilled in the art. Preferably, the separation is performed at a pH of about 2 to about 4. More preferably, electrophoresis is carried out at a pH of 2.5

14 Claims, 3 Drawing Sheets

OTHER PUBLICATIONS

Anthony T. Andrews, Food Research Institute, Reading, Electrophoresis, Theory, Techniques, and Biochemical and Clinical Applications, Second Edition, Clarendon Press Oxford 1986, p. 188–, 243.

James B Herrick et al, Polymerase Cain Reaction Amplification of Naphthalene–Catabolic and 16S rRNA Gene Sequences from Indigenous Sediment Bacteria; Applied and Environmental Microbiology, Mar. 1993, p. 687–694, vol. 59, No. 3.

Andrews; Electrophoresis Theory, Techniques, and Biochemical and Clinical Applications; 1986; Introduction 1.1–2.1 and pp. 1–5, 188–203 Only.

Young, Burghoff, Keim, Minak–Bernero, Lute, and Hinton; Applied and Environmental Microbiology, Jun. 1993, vol. 59. No. 6; pp. 1972–1974.

Edward L. Sheldon, Ph. D.; Pre–Conference Workshop–Monday, Jun. 9, 1997; Automated DNA Sample Preparation (Abstract).

* cited by examiner

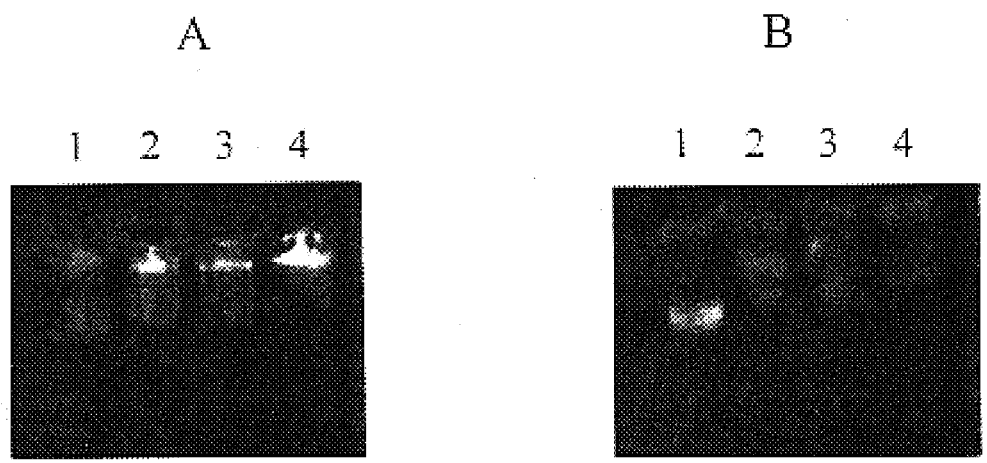
Figure 1. Electrophoresis of nucleic acids on agarose gels at pH 2.5. One percent agarose gels were prepared and run in: A. 3 mM HCl, or B. 50 mM glycine-HCl, pH 2.5. Lane 1, calf thymus DNA; lane 2, pTRI-Xef transcript; lane 3, 16 S – 23 S rRNA; lane 4, 5 S rRNA; 0.5 ug nucleic acid per lane.

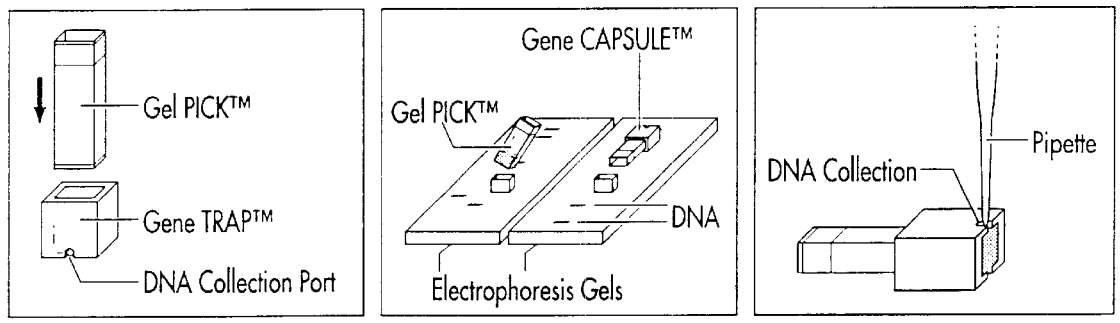
Figure 2. Use of Gene*CAPSULE* for electroelution of nucleic acids and proteins from agarose and acrylamide gels. Taken from GenoTechnology's (St. Louis, MO) promotional literature. Intended and actual use as described in the text for Example 2.

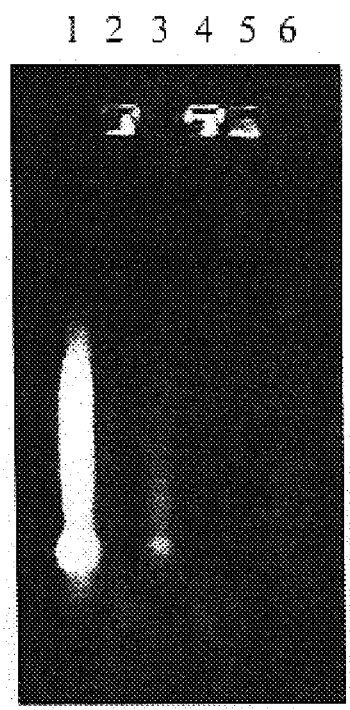
Figure 3. Recovery of rRNA after electrophoresis at pH 2.5 in GeneCAPSULE. A 1% agarose gel was prepared and run in TBE, as described in the text. Lane 1, 1 ug each of 23 S, 16 S, & 5 S rRNA; lanes 2-6 equal proportions of fractions from GeneCAPSULE, as listed in Table 1.

ELECTROPHORETIC SEPARATION OF NUCLEIC ACIDS FROM PROTEINS AT LOW PH

This application claims priority from provisional application No. 60/095,258 filed Aug. 4, 1998.

FIELD OF THE INVENTION

The present invention relates generally to methods of separating nucleic acids from cellular debris, such as proteins, in a biological sample. Specifically, the invention relates to the use of electrophoresis at a low pH to separate nucleic acids from substances carrying a net positive charge.

BACKGROUND INVENTION

Technology to detect minute quantities of nucleic acids has advanced rapidly over the last two decades including the development of highly sophisticated amplification techniques such as polymerase chain reaction (PCR). Researchers have readily recognized the value of such technologies to detect diseases and genetic features in human or animal test specimens.

PCR is a significant advance in the art to allow detection of very small concentrations of a targeted nucleic acid. The details of PCR are described, for example, in U.S. Pat. No. 4,683,195 (Mullis et al), U.S. Pat. No. 4,683,202 (Mullis) and U.S. Pat. No. 4,965,188 (Mullis et al), although there is a rapidly expanding volume of literature in this field. Without going into extensive detail, PCR involves hybridizing primers to the strands of a targeted nucleic acid (considered "templates") in the presence of a polymerization agent (such as DNA polymerase) and deoxyribonucleoside triphosphates under the appropriate conditions. The result is the formation of primer extension products along the templates, the products having added thereto nucleotides which are complementary to the templates.

Once the primer extension products are denatured, and one copy of the templates has been prepared, the cycle of priming, extending and denaturation can be carried out as many times as desired to provide an exponential increase in the amount of nucleic acid which has the same sequence as the target nucleic acid. In effect, the target nucleic acid is duplicated (or "amplified") many times so that it is more easily detected.

In order to effectively amplify and detect a target nucleic acid or to clone or sequence a target nucleic acid, it is frequently necessary to isolate or separate the nucleic acid from a mixture of other interfering biomolecules. (Moore D., 1997. Preparation and Analysis of DNA. Unit 2.2 In Ausubel et al. (ed.), Current Protocols in Molecular Biology. John Wiley & Sons, Inc., New York.)

Presently, several different procedures are used to remove proteins and other impurities from nucleic acid preparations. Traditionally, biological samples were digested with a protease, and impurities removed from the nucleic acids by organic extraction (Moore D., Current Protocols in Molecular Biology). This method, however, has several recognized disadvantages including using hazardous organic solvents and requiring several transfers of aqueous phase to fresh tubes, which is tedious, labor intensive, and adds to the risk of cross contaminating samples.

Purification of nucleic acids by adsorption to glass in a chaotropic salt has become popular more recently (Boom et al., 1990, J. Clinical Microbiol. 28:495–503). However, this separation method also suffers from several disadvantages including using glass that has a very low binding capacity, employing chaotropic salts, and being tedious and time consuming because the glass-nucleic acid complex must be washed several times and the wash solution removed.

Polymer capture, an ion exchange procedure, to purify DNA has also been employed to isolate nucleic acids (U.S. Pat. Nos. 5,582,988, 5,434,270, and 5,523,368). Unfortunately, such procedures are not particularly suitable for RNA purification under the conditions currently practiced because RNA would be degraded both during capture and release. Under optimal polymer-nucleic acid capture conditions ribonuclease activity would be high resulting in degradation of the RNA and the high pH needed to release nucleic acids from the polymer would result in chemical hydrolysis.

Electrophoretic separation is an appealing technique because such procedures can be designed to avoid hazardous substances, high pH, and tedious manipulations. In addition, electrophoretic separation is readily adaptable to automated formats. Although electrophoresis is most often used on an analytical scale, many small-scale preparative procedures have been developed as well (Andrews, A. T., 1986, Electrophoresis: Theory and Techniques, and Biochemical and Clinical Applications, 2nd edition. Clarendon Press, Oxford, England). Procedures have also been reported that separate DNA from humic materials and other impurities that inhibit PCR by electrophoresis on polyvinylpyrrolidone-agarose gels (Herrick et al., 1993, Appl. Environ. Microbiol. 59:687–694 and Young et al., 1993, Appl. Environ Microbiol., 59:1972–1974). In addition, Sheldon and co-workers developed a device for electrophoretic purification of nucleic acids. Cells or blood samples are lysed with a protease and the lysate is loaded into the device. Nucleic acids are separated from impurities by electrophoresis through a polymer layer and are retained in a collection chamber by a molecular weight cut-off membrane, while degraded proteins and other low molecular weight substances pass through the membrane (Sheldon E. L., 1997. Electronic Sample Handling. Presented at International Business Preparation Workshop. San Diego, Calif., Jun. 9, 1997).

Although most electrophoretic separations are run at a pH close to neutral, including those examples mentioned above, electrophoresis at low pH is sometimes advantageous. For example, some macromolecules separate more efficiently at low pH. Mixtures of nucleotides or low molecular weight polynucleotides separate better at low pH because the charge on nucleotides varies from negative 1 to 0 between pH 2 and 5, while most have the same charge (minus 2) between pH 6 and 8 (Smith, J. D., 1976, Methods Enzymol. 12:350–361). Similarly, with isoelectric focusing, acidic proteins are isolated at their pKa in a pH gradient (Andrews, A. T., 1986). In addition, some structures are more stable at low pH. Terwillinger and Clarke reported that acidic conditions (pH 2.5) help minimize hydrolysis of protein methyl esters during electrophoresis (Terwillinger et al., 1981, J. Biol. Chem. 256:3067–75). Similarly, triple helix structures of B-DNA are stabilized by mild acid conditions (pH 4.5) (Mirkin et al., 1987, J. Biol. Chem. 234:1512–16).

Accordingly, it would be desirable and advantageous to be able to use low pH conditions for preparative electrophoresis of nucleic acids, especially from protein-rich sources such as blood or plasma. Nucleases, especially ribonucleases, which are ubiquitous and will degrade nucleic acids during electrophoresis, are inactivated at low pH (Kalnitsky et al., 1959, J. Biol. Chem. 234:1512–16). Furthermore, most nucleic acids and proteins will have opposite charges under acid conditions, and therefore, will migrate in opposite directions in an electric field. At pH 2, nucleic acids will still be negatively charged, because the pKa values of the primary phosphate groups are less than 2 while those of the amine groups are between 2 and 5 (Smith, J. D., 1976). On the other hand, most proteins will be fully protonated, and therefore, positively charged because the pKa's for all the amine and most carboxyl groups of proteins are much greater than 2.

SUMMARY OF THE INVENTION

Accordingly, the present invention overcomes the above-noted problems and provides a needed means for separating nucleic acids from substances that carry a net positive charge at low pH by electrophoresis under acid conditions. Electrophoresis at low pH also overcomes many of the problems with current methods for nucleic acid purification. As mentioned above, nucleases are less active at low pH, so the nucleic acids would be more stable than at neutral pH. Furthermore, once samples are loaded, electrophoresis is a hands-off method. Finally, no hazardous materials are needed.

Various other objects and advantages of the present invention will be apparent from the detail description of the invention.

BRIEF DESCRIPTION OF THE DRAWINGS

FIG. 1 shows the results of electrophoresis of nucleic acids on agarose gels at pH 2.5. One percent agarose gels were prepared and run in: A. 3 mM HCl, or B. 50 mM glycine-HCl, pH 2.5. Lane 1, calf thymus DNA; lane 2, pTRI-Xef transcript; lane 3, 16S+23S rRNA; lane 4, 5 S rRNA; 0.5 ug nucleic acid per lane.

FIG. 2 illustrates the use of GENECAPSULE for electroelution of nucleic acids and proteins from agarose and acrylamide gels. Taken from GenoTechnology's (St. Louis, Mo.) promotional literature.

FIG. 3 shows the recovery of rRNA after electrophoresis at pH 2.5 in GENECAPSULE. A 1% agarose gel was prepared and run in TBE, as described in the Examples. Lane 1, 1 ug each of 23S, 16S and 5S rRNA; lanes 2–6 equal proportions of fractions from GENECAPSULE, as listed in Table 1.

DETAILED DESCRIPTION OF THE INVENTION

The present invention relates to methods for separating nucleic acids from other cellular debris, especially substances that carry a net positive charge at low pH, by electrophoresis under acid conditions. In the purification method of the present invention, nucleic acids are separated from proteins found in the same biological sample by applying the sample to an electrophesis gel and subjecting the sample to electrophoresis under acid conditions to separate the nucleic acids from the proteins. The optimum pH may differ for different sample types but can be readily determined by those skilled in the art. Preferably, the separation is performed at a pH of about 2 to about 4. More preferably, electrophoresis is carried out at a pH of 2.5.

At a pH between approximately 2 and 4, most nucleic acids will carry a net negative charge due to the low pKa of phosphate groups, whereas most proteins will have a net positive charge because their functional groups (amino and carboxyl groups) have much higher pKa's. As a consequence, most nucleic acids and proteins will migrate in opposite directions during electrophoresis at a pH of about 2 to 4. This approach differs from current procedures for preparative electrophoresis of nucleic acids, which are run at a pH where nucleic acids and proteins migrate in the same direction (towards the anode). More complete and efficient separation should be achieved when molecules move in opposite directions.

Sample pH should be adjusted before applying the sample to the gel because pH shift needs to rapidly and efficiently inhibit $RNA_{ase}$ activity. Suitable reagents for use in the present invention to achieve an acid pH include, but are not limited to, HCl, glycine-HCl, sulfuric or phosphoric acids, and other buffers, such as phosphate, pthalate, fumarate, tartrate, citrate, glycylglycine, furoate, or formate.

Various devices and formats can be used to practice the present invention. While the GENECAPSULE™ is used in the following examples, other preassembled, direct injection devices would also be suitable. Furthermore, preparative isoelectric focusing, especially with immobilized pH gradients (Righetti and Wenisch, 1997, Preparative Isoelectric Focusing Using Immobilized Membranes: Theory and History. IsoPrime Application Note; No. 1 Hoefer Scientific Instruments.), could be used to give a clean separation of the molecules of interest from impurities than are obtained with electrophoresis through an homogenous matrix.

The separation method of the present invention offers several advantages over traditional methods for nucleic acid purification including an absence of hazardous materials, tedious transfers, or extractions. In addition, with electrophoresis under acid conditions (pH≦3) instead of at a pH close to neutral, nucleases are essentially inactive and RNA is chemically more stable. Moreover, under acid conditions, such as pH 2.5, nucleic acids and most proteins will migrate towards opposite electrodes for more efficient and complete separation.

Once the nucleic acids are separated from the proteins found in the biological sample, the electric field is removed and the separated nucleic acids can be removed from the gel using techniques well known in the art. Such purified nucleic acids are then suitable for use in standard amplification and/or detection technologies, such as PCR and ligase chain reaction.

The general principles and conditions for amplification and detection of nucleic acids using PCR are quite well know, details of which are provided in numerous references, including U.S. Pat. No. 4,683,195 (Mullis et al.), U.S. Pat. No. 4,683,202 (Mullis), and U.S. Pat. No. 4,965,188 (Mullis et al.), all of which are incorporated herein by reference. Thus, in view of the teachings in the art and the specific teachings provided herein, one skilled in the art should have no difficulty in practicing the present invention to eliminate false negative results which would be due to the presence of applification inhibitors or due to inefficient recovery of intact RNA or DNA in amplification assays.

The term "biological sample" includes, but is not limited to, cellular or viral material, hair, body fluids or cellular material containing nucleic acids which can be detected.

The method described herein can be used to detect specific nucleic acid sequences associated with infectious diseases, genetic disorders or cellular disorders such as cancers or any other disease states not specifically included in these categories. It may also be used in forensic investigations and DNA typing. For purposes of this invention, genetic diseases include specific deletions or mutations in genomic DNA from any organism, such as sickle cell anemia, cystic fibrosis, α-thalassemia, β-thalassemia and others readily apparent to one skilled in the art. Human Leukocyte Antigen (HLA) can be categorized with the present invention. Bacteria which can be detected include, but are not limited to, bacteria which may be found in the blood, Salmonella, Streptococcus species, Chlamydia species, Gonococcus species, mycobacteria species (such as *Mycobacterium tuberculosis* and *Mycobacterium avium* complex), Mycoplasma species (such as Mycoplasma *Haemophilus influenzae* and *Mycoplasma pneumoniae*), *Legionella pneumophila, Borrelia burgdorferei, Pneumocystis carinii, Clostridium difficile*, Campylobacter species, Yersinia species, Shigella species and Listeria species. Viruses which are detectable include, but are not limited to, herpes simplex viruses, Epstein Barr virus, respiratory syncytial viruses, hepatitis viruses and retroviruses syncytial viruses, hepatitis viruses and retroviruses (such as HTLV-I, HTLV-II, HIV-I and HIV-II). Protozoan parasites and fungi (including yeasts and molds) are also detectable. Other detectable species would be readily apparent to one skilled in the art. The invention is particularly useful for the detection of the presence of RNA associated with various bacteria or viruses.

EXAMPLES

Materials

Hydrochloric acid was reagent grade from Baker. Glycine (molecular biology grade), calf thymus DNA, 5S rRNA from *E. Coli*, and 16S+23S rRNA from *E. Coli* were from Sigma Chemical Co. (St. Louis, Mo.). The pTRI-Xef1 transcript was synthesized from Ambion's (Austin, Tex.) pTRI-Xef1 plasmid with Ambion's Megascript in vitro transcription system according to the manufacturer's instructions. Agarose was SeaKem LE from FMC Bioproducts (Rockland, Me.). The GENECAPSULE electroelution device, from GenoTechnology (St. Louis, Mo.), was used to separate RNA from protein by modifying the manufacturer's instructions, as described in Example 2 below. Protein levels were determined with Pierce's (Rockford, Ill.) BCA Protein Assay Reagent kit according to the manufacturer's instructions.

Example 1

To verify that nucleic acids will migrate towards the anode during electrophoresis under acid conditions, 1% agarose gels were prepared and run in either 3 mM HCl or 50 mM glycine-HCl, both at pH 2.5. Half microgram samples of calf thymus DNA (FIG. 1, lane 1), a 1.9 kb mRNA (pTRI-Xef1 transcript; lane 2), 16S+23S rRNAs from *E. Coli* (lane 3), and 5S rRNA from *E. Coli* (lane 4) were loaded into wells at the cathode ends of the gels, and subjected to 100 V for 15 min. The gels were stained with ethidium bromide, and photographed with UV transillumination.

As shown in FIG. 1, both the DNA and the three RNAs moved away from the cathode and towards the anode in either HCl (panel A) or glycine-HCl (panel B) at pH 2.5. Therefore, these nucleic acids maintain a net negative charge at pH 2.5.

Example 2

To demonstrate that nucleic acids and proteins migrate in opposite directions during electrophoresis under acid conditions, rRNA was separated from blood plasma proteins in a modified GENECAPSULE device (FIG. 2). These devices were designed to elute DNA, RNA, or proteins from agarose or polyacrylamide gel slices by electrophoresis. According to the manufacturer's intended use, a piece of gel containing a nucleic acid or protein band of interest is picked up into the GENE PICK, then the GENE PICK is filled with agarose gel and assembled with a GENE TRAP. The GENE TRAP has a membrane (probably dialysis membrane) at one end that lets electrons through, but traps the macromolecules. The assembled GENECAPSULE is submerged in electrophoresis buffer with the trap towards the anode, and the nucleic acid or protein is eluted by electrophoresis into residual buffer (25–40 µl) in the trap next to the membrane.

For the purposes of this experiment, a mixture of blood plasma and rRNAs were cast in agarose in the GENE PICK, and the GENE PICK was assembled with a GENE TRAP at both ends to capture macromolecules that migrate either direction. To accomplish this, one end of a GENE PICK was plugged with parafilm. Agarose was dissolved in 110 mM glycine-HCl, pH 2.5, at 2.2% by boiling, and 250 µl aliquots were placed at 50–60 C. to prevent the agarose from hardening. To the molten agarose were added 100 µl of blood plasma, 200 µl of 80 mM HCl, and 20 µg each of 5S, 16S, and 23S rRNA from *E. Coli*, which yields final concentrations of 1% agarose and 50 mM glycine-HCl at pH 2.5. The mixture was vortexed and immediately pipetted into the plugged GENE PICK. One hundred µl of 50 mM glycine-HCl was added to both traps, and these were assembled with the pick while held at an angle to expel bubbles. One percent agarose in water was used to seal the traps to the pick. The assembled GENECAPSULE was submerged in 50 mM glycine-HCl in a horizontal electrophoresis chamber, and subjected to 100 V for 1 hr. The current was reversed for 60 sec, as recommended by the manufacturer to release RNA from the membrane. The GENECAPSULE was removed from the electrophoresis buffer, and residual buffer next to the membrane was removed from both traps according to the manufacturer's instructions. In a preliminary experiment, it was discovered that some of the RNA and protein remained adsorbed to the trap membranes even after the current was reversed for 60 sec. Therefore, the membranes were removed from the traps and eluted in 100 µl of 50 mM glycine-HCl, pH 2.5 for 1 hr at 37 C. Also, the agarose gel was removed from the trap, melted, and analyzed for residual RNA and protein as well. Each fraction was checked for the presence of RNA by running equal proportions on a standard 1% agarose gel in 1×TBE (89 mM Tris-borate, 2 mM EDTA). In addition, aliquots of each fraction were assayed for protein content.

As shown in Table 1, protein was detected in the agarose gel (row 4) or at the cathode, or negative end of the GENECAPSULE, either in the trap (row 2) or on the membrane (row 5). Only 5% of the total protein recovered was found at the anode, or positive end (rows 3 & 6). On the other hand, as shown on the agarose gel in FIG. 3, RNA was detected only at the anode, or positive end of the GENECAPSULE, either in the trap (lane 3) or on the membrane (lane 6). Only a portion of the RNA was recovered, as determined by comparing intensities with total RNA in lane 1. It is likely that the bulk of the RNA was adsorbed onto the GENECAPSULE or left on the positive membrane. However, none was detected at the cathode, or negative end where the protein was found (lanes 2 & 5). Therefore, these nucleic acids and proteins did indeed migrate in opposite directions during electrophoresis at pH 2.5.

TABLE 1

Recovery of Plasma Protein from GENECAPSULE

| Row (lane) | Fraction | Protein (mg) |
|---|---|---|
| 1 | whole plasma | 7.7 |
| 2 | negative trap | 1.0 |
| 3 | positive trap | 0.2 |
| 4 | agarose gel | 1.5 |
| 5 | negative membrane | 1.6 |
| 6 | positive membrane | 0.02 |
|  | total recovered | 4.3. |

The present invention has been described in detail with particular reference to preferred embodiments thereof, but it will be understood by those skilled in the art that variations and modifications can be effected within the spirit and scope of the invention.

All publications mentioned hereinabove are hereby incorporated by reference.

What is claimed:

1. A method for preparative electrophoesis of RNA comprising separation of the RNA from a biological sample consisting of hair or body fluids, consisting essentially of the steps of:
   (a) applying the biological sample containing RNA to a medium having a pH between about 2 to about 4;
   (b) subjecting the sample in said acid medium to an electric field means; and
   (c) separating the RNA in the biological sample.

2. The method of claim 1 wherein the pH is pH 2.5.

3. The method of claim 1 wherein the electrical field means comprises electrophoresis.

4. The method of claim 1, wherein the body fluids consists of blood plasma.

5. A method of separating nucleic acid from a biological sample consisting of hair or body fluids consisting essentially of:
   (a) applying the biological sample to an acid medium at pH 2–4;
   (b) subjecting the sample in said acid medium to an electric field means; and
   (c) separating the nucleic acids in the acid medium from the biological sample.

6. The method of claim 5 wherein the body fluids consists of blood plasma.

7. The method of claim 5 wherein the electric field means is electrophoresis.

8. The method of claim 5 wherein the pH is about 2 to about 3.

9. The method of claim 5 wherein the pH is about 2.5.

10. A method of separating RNA from a biological sample consisting of hair or body fluids consisting essentially of:
    (a) applying the biological sample to an acid medium at pH 2–4;
    (b) subjecting the sample in said acid medium to an electric field means; and
    (c) separating the RNA in the acid medium from the biological sample.

11. The method of claim 10 wherein the body fluids consists of blood plasma.

12. The method of claim 10 wherein the electric field means is electrophoresis.

13. The method of claim 10 wherein the pH is about 2 to about 3.

14. The method of claim 10 wherein the pH is about 2.5.

* * * * *